United States Patent
Emanuel (10) Patent No.: US 7,595,020 B2
(45) Date of Patent: Sep. 29, 2009

(54) METHOD OF TREATING BIOLOGICAL AND CHEMICAL AGENTS WITH GAS PHASE, ELECTRONICALLY EXCITED STATES OF OXYGEN

(75) Inventor: George Emanuel, Arlington, TX (US)

(73) Assignee: KSY Corporation, Arlington, TX (US)

( * ) Notice: Subject to any disclaimer, the term of this patent is extended or adjusted under 35 U.S.C. 154(b) by 832 days.

(21) Appl. No.: 10/795,715

(22) Filed: Mar. 8, 2004

(65) Prior Publication Data

US 2004/0170545 A1 Sep. 2, 2004

Related U.S. Application Data (63) Continuation-in-part of application No. 10/453,148, filed on Jun. 3, 2003, now Pat. No. 7,116,696.

(60) Provisional application No. 60/387,539, filed on Jun. 10, 2002.

(51) Int. Cl.
| | |
|---|---|
| A62B 7/08 | (2006.01) |
| A61L 9/00 | (2006.01) |
| B01J 19/08 | (2006.01) |
| A61L 2/00 | (2006.01) |
| A62C 31/00 | (2006.01) |
| B05B 7/04 | (2006.01) |
| B05B 7/08 | (2006.01) |
| C02F 1/76 | (2006.01) |
| C02F 1/72 | (2006.01) |
| C02F 1/68 | (2006.01) |
| H01S 3/22 | (2006.01) |
| A24B 1/02 | (2006.01) |

(52) U.S. Cl. .......................... 422/28; 422/120; 422/305; 422/22; 422/121; 422/186; 422/37; 422/122; 239/589; 239/601; 239/398; 239/426; 239/433; 239/434; 210/753; 210/758; 210/764; 375/55; 375/88; 375/89; 375/90; 432/579

(58) Field of Classification Search ......... 422/120–122, 422/305, 22, 28, 186, 37; 239/589, 601, 239/398, 426, 433, 434; 210/753, 758, 764; 423/579; 372/55, 88–90; 432/579
See application file for complete search history.

(56) References Cited

U.S. PATENT DOCUMENTS 4,318,895 A * 3/1982 Richardson et al. .......... 423/579

(Continued)

FOREIGN PATENT DOCUMENTS

WO    WO 03/104145 A1    12/2003

OTHER PUBLICATIONS

Alrano, A.J. And Christe, K.O., "Singlet Delta Oxygen Production from a Gas-Solid Reaction," Angew. Chem. Int. Ed. 41(17, 3252-3254), 2002.

(Continued)

*Primary Examiner*—Jill Warden
*Assistant Examiner*—Monzer R Chorbaji
(74) *Attorney, Agent, or Firm*—Storm LLP; Paul V. Storm; Mark D. Perdue (57) ABSTRACT

An improved singlet oxygen generator (SOG) and method of using gas phase electronically excited states of oxygen for bio-medical and chemical treatment applications are disclosed. According to the invention, both gas phase $O_2(^1\Sigma)$ and $O_2(^1\Delta)$ are used for medical treatment, sterilization, and deactivation of biological and chemical agents, including diseased tissue and biological and chemical weapons. The improved SOG is compact and scalable, portable, capable of operating in a zero-gravity or low gravity environment, may use gaseous diluent or buffer gas, and is capable of operating at pressures as high as one atmosphere. The SOG is capable of operating within a short distance of the target site for the electronically excited states of oxygen, which are delivered to the target site via a conduit. The SOG and delivery system provide higher yields of electronically excited oxygen with longer lifetimes suitable for bio-medical applications.

23 Claims, 3 Drawing Sheets

U.S. PATENT DOCUMENTS

| | | | | |
|---|---|---|---|---|
| 4,407,282 | A | * | 10/1983 | Swartz .................... 604/20 |
| 4,640,782 | A | | 2/1987 | Burleson et al. |
| 5,229,100 | A | * | 7/1993 | Harpole .................. 423/579 |
| 5,417,928 | A | * | 5/1995 | McDermott ............. 422/120 |
| 5,516,502 | A | * | 5/1996 | Dickerson ............... 423/579 |
| 5,607,924 | A | | 3/1997 | Magda et al. |
| 6,072,820 | A | | 6/2000 | Dickerson |
| 6,551,346 | B2 | * | 4/2003 | Crossley ................. 607/88 |
| 6,630,105 | B1 | * | 10/2003 | O'Neill et al. ........... 422/24 |

OTHER PUBLICATIONS

Rybalkin, V. et al., "Nearly attaining the theoretical efficiency of supersonic chemical oxygen-iodine lasers," Applied Physics Letters, vol. 85, No. 24, pp. 5851-5853 (Dec. 13, 2004).

Endo, M., et al., "Development of Hybrid Simulation for Supersonic Chemical Oxygen-Iodine Laser," AIAA Journal, vol. 45, No. 1, pp. 90-97 (Jan. 2007).

* cited by examiner

METHOD OF TREATING BIOLOGICAL AND CHEMICAL AGENTS WITH GAS PHASE, ELECTRONICALLY EXCITED STATES OF OXYGEN

CROSS REFERENCE TO RELATED APPLICATIONS

The present application claims priority as a continuation-in-part application of U.S. Provisional Application Ser. No. 60/387,539, filed on Jun. 10, 2002 and U.S. patent application Ser. No. 10/453,148, filed on Jun. 3, 2003, now U.S. Pat. No. 7,116,696 both titled Efficient Method and Apparatus for Generating Singlet Delta Oxygen at an Elevated Pressure.

TECHNICAL FIELD

The present invention relates generally to an improved method and apparatus for generating gas-phase electronically excited singlet states of oxygen and the use of these excited oxygen states for medical and other applications, particularly the treatment of diseased tissue, sterilization of equipment and instruments, and deactivation of biological and chemical weapons.

BACKGROUND OF THE INVENTION

A recent, increasingly important, treatment method for solid tumors is photodynamic therapy. Singlet oxygen, which in the prior art refers to singlet delta oxygen or $O_2(^1\Delta)$, is released in the tumor where it can destroy diseased tissue. Prior art treatment methods utilize singlet oxygen in solution, rather than in the gas phase.

In the biomedical prior art, there are two general methods for the generation of $O_2(^1\Delta)$. In the first, an aqueous solution is used, such as a mixture of hydrogen peroxide with a hypochloride. Since the lifetime of $O_2(^1\Delta)$ in an aqueous solution is quite short, the $^1\Delta$ molecule must be generated very close to, or at, its target site.

In the second prior art biomedical method, the $O_2(^1\Delta)$ is generated by the photoirradiation of a large parent molecule, such as a metal complex of a texaphyrin compound. Photodynamic therapy uses this approach, in which a patient is infused with a compound that is supposed to migrate to, and be absorbed at, the site of cancerous tissue. Upon optical irradiation of the tumor site, the compound releases $O_2(^1\Delta)$, which can then destroy the diseased tissue.

Singlet oxygen has also been shown to disrupt platelet aggregates. Singlet oxygen, along with the hydroxyl radical, superoxide, and peroxides, are also causative agents of skin diseases and of aging of the skin. Of the above active oxygen-containing molecules, singlet delta is the most reactive.

Electronic states of oxygen can also be generated by an electric discharge or by a microwave discharge. The result is generally a hot gas mixture of various internally- and electronically-excited states and ions that, in general, are not suited for medical, or medical-related, applications.

This invention relates to a method and apparatus for generating and delivering electronically excited states of oxygen in the gas-phase at or near room temperature, that is suitable for biomedical related applications, such as for the treatment of tumors and sterilization of instruments and equipment. According to the invention, both singlet delta oxygen, $O_2(^1\Delta)$, and singlet sigma oxygen, $O_2(^1\Sigma)$, are generated by an external source and may be used for the treatment of tumors, hardware and instrument sterilization, and deactivation of chemical and biological weapons and contaminants.

The lowest two electronically excited states of diatomic oxygen are $a^1\Delta_g$ (or $O_2(^1\Delta)$) and $b^1\Sigma_g^-$ (or $O_2(^1\Sigma)$). The a-state is 94.2 kJ/mol above the electronic ground state, $X^3\Sigma_g^-$, while the b-state is 157 kJ/mol above the ground state. The b-state is thus appreciably more energetic than the a-state. For convenience, these three states are referred to as $^3\Sigma$, for the ground state, $^1\Delta$, for the lowest electronic state, and $^1\Sigma$, for the next highest electronic state. Both the $^1\Delta$ and $^1\Sigma$ states are singlet states. In the prior art, however, the phrase "singlet oxygen" typically refers to the $^1\Delta$ state.

The use of electronically excited oxygen in the gas phase according to the invention is advantageous over the prior art use of $O_2(^1\Delta)$ in solution. The gas-phase excited states have a much longer lifetime than in aqueous solution, which has been used in the prior art. As a gas, it can penetrate cracks and fissures. Also the use of the more energetic electronic state, $O_2(^1\Sigma)$, according to the invention may be more effective in destroying diseased tissue than $O_2(^1\Delta)$. Other applications of gas-phase, electronically excited oxygen, including the $^1\Delta$ and $^1\Sigma$ states, according to the invention include sterilization of hardware, medical instruments and passageways or ducts used for the transport of air and other fluids. This also includes the sterilization of biofilms, which are difficult to destroy with conventional sterilization techniques, and which can be present on pacemakers, catheters, and other medical instruments. Due to its extreme reactivity, the use of gaseous excited oxygen should be efficient in deactivating a broad spectrum of the active compounds in chemical and biological weapons.

When $O_2(^1\Delta)$ is generated in the liquid phase, it has a lifetime of about two microseconds. In the gas phase, however, the radiative lifetime of $O_2(^1\Delta)$ is about 71 minutes. It will actually be less in the gas phase because of collisional deactivation processes. The most important homogeneous deactivation paths for $^1\Delta$ are the two binary reactions $$2O_2(^1\Delta) \leftrightarrow O_2(^1\Sigma) + O_2(^3\Sigma) \qquad \text{Reaction A}$$

$$2O_2(^1\Delta) \rightarrow 2O_2(^3\Sigma) \qquad \text{Reaction B}$$

where Reaction A is referred to as the pooling reaction. Reaction B is responsible for the readily visible red dimol emission that occurs when $^1\Delta$ is in the gas phase. At room temperature, the pooling reaction is slightly faster than the dimol reaction; the branching ratio favoring the pooling reaction is about 61.4%. The backward rate for Reaction A is appreciable and becomes significant when the $^3\Sigma$ and $^1\Sigma$ concentrations become appreciable. Because of the red emission, the backward rate for Reaction B is considered negligible.

The invention also relates to an improved method and apparatus for generating the electronically excited states of diatomic oxygen, $O_2(^1\Delta)$ and $O_2(^1\Sigma)$, in vapor form. The external apparatus for generating excited oxygen is referred to as a singlet oxygen generator or SOG. As used to describe the invention, a singlet oxygen generator or SOG refers to a device for generating $O_2(^1\Delta)$, such as by reaction of basic hydrogen peroxide (BHP) and chlorine, and generating $O_2(^1\Sigma)$, such as by Reaction A.

Singlet delta oxygen is generally produced by reacting aqueous BHP with chlorine, while $O_2(^1\Sigma)$ is produced by the reaction of two $O_2(^1\Delta)$ molecules. When $O_2(^1\Delta)$ is chemically generated, the $O_2(^1\Sigma)$ state occurs only as a result of Reaction (A). When generated in the liquid phase, the lifetime of the $^1\Sigma$ is much less than one microsecond. This extremely short lifetime for the $^1\Sigma$ state in the liquid phase is likely the reason why the biomedical related prior art has not considered use of the $^1\Sigma$ state. In the gas phase, the rate of deactivation of $^1\Sigma$ by water vapor is significant, and represents the dominant deactivation mechanism for $^1\Sigma$. The rate of $O_2(^1\Sigma)$ deactivation is sharply reduced with the use of deuterated water in place of $H_2O$ in the aqueous BHP solution. The production of $O_2(^1\Sigma)$ by Reaction A continues to occur in the gas phase downstream of the BHP solution, where the $O_2(^1\Delta)$ is generated. As long as $O_2(^1\Delta)$ is present, $O_2(^1\Sigma)$ is produced.

Aqueous BHP is produced by mixing liquid water with an aqueous solution of hydrogen peroxide ($H_2O_2$) and an aqueous solution of potassium hydroxide (KOH). Alternatively, sodium hydroxide (NaOH) may be used in place of KOH. In the BHP solution, the $H_2O_2$ and KOH exist as various ionic molecules. The mixing and reactive process in making BHP is exothermic.

When BHP is mixed with chlorine, the following stoichiometric chemical reaction takes place:

$$H_2O_2 + KOH + Cl_2 \rightarrow KCl + H_2O + HCl + O_2 \quad \text{Reaction C}$$

where the oxygen is in its lowest energy electronically excited state. For convenience, this is referred to as singlet delta oxygen or as $O_2(^1\Delta)$. Normally, oxygen is in its electronic ground state, $O_2(X^3\Sigma_g^-)$, which, hereafter, is written as $O_2(^3\Sigma)$ or just $O_2$. In Reaction C, the chlorine vapor diffuses into the aqueous BHP solution, ultimately forming potassium chloride (KCl), or sodium chloride (NaCl) if NaOH is used in the reaction, water, HCl, and $O_2(^1\Delta)$. The $O_2(^1\Delta)$ can form bubbles and diffuse out of the solution.

Various types of singlet delta oxygen generators have been developed in the prior art. These generators typically generate singlet delta oxygen in the gas phase for use in the Chemical Oxygen-Iodine Laser (COIL). These generators typically use BHP with chlorine and a diluent gas, such as helium. Optimum singlet delta oxygen production occurs when the $H_2O_2$ molar flow rate is slightly in excess of the KOH, or NaOH, molar flow rate. These molar flow rates were used in the feasibility experiment according to the invention described later.

One type of prior art SOG uses a transverse flow uniform droplet method in which BHP droplets, ranging in size from 0.4 mm to 0.5 mm (15.8 mil to 19.7 mil) diameter, fall under the influence of gravity into a sump. Chlorine vapor and a diluent gas flow across the path of the droplets. The flow speed of the chlorine vapor and diluent is limited, otherwise the droplets would be transported downstream with the diluent and the generated oxygen. There is an adverse trade-off in that the maximum vapor speed, which includes the generated singlet delta oxygen, must decrease as the droplet size decreases. Generator pressures of around 92 Torr (0.12 atm), most of which is due to helium diluent, have been reported in this type of SOG. The partial pressure of the generated oxygen reported for this type of SOG is only around 14.3 Torr (0.02 atm).

Another type of prior art SOG is a verticoil oxygen generator. In this device, a number of disks rotate such that the lower portion of the disks is in a BHP sump. The upper portion of the disks is thus wetted with a BHP film. Chlorine vapor and diluent flow past the upper part of the disks to react with the BHP film. Generator pressures of about 40 Torr (0.05 atm), most of which stems from the helium diluent that enters the reactor with the chlorine vapor, have been reported in this type of SOG.

Another type of prior art SOG is a twisted-flow aersol-jet singlet oxygen generator. A partial pressure of about 75 Torr (0.1 atm) of singlet delta oxygen has been reported for this type of generator, but this $O_2(^1\Delta)$ pressure decreases, to around 22.5 Torr (0.03 atm), at the nozzle inlet for a laser. This significantly decreases the laser efficiency.

Another method for generating gas-phase $O_2(^1\Delta)$ from the reaction of gaseous hydrogen (deuterium) halides and solid peroxides has been disclosed in Alfano, A. J. and Christe, K. O., "Singlet Delta Oxygen Production from a Gas-Solid Reaction," Angew. Chem. Int. Ed. 41(17, 3252-3254 (2002). The objective is to provide gas-phase $^1\Delta$ for COIL. Whether the application is that of a laser or for other uses, one drawback is the difficulty with this approach in separating $^1\Delta$ from the halide gas.

The foregoing prior art SOGs have, in common, a number of adverse characteristics:

(a) The devices are bulky, and typically require large diameter ducting (because of the low density) to transport the $O_2(^1\Delta)$ stream to the desired endpoint.

(b) Primarily, because of Reactions A and B, the singlet delta oxygen partial pressure entering the inlet of the laser's nozzle (or other point of application depending on the use) has not exceeded about 22.5 Torr (0.03 atm) in prior art systems. To increase the pressure in the generator, a diluent gas is used, typically helium or nitrogen. The need for supply tanks, plumbing, etc., to accommodate the use of a diluent gas further increases the size and weight of the overall system. Even with diluent, however, the total pressure inside the SOG is still well below 1 atm, typically below about 175 Torr. With an $O_2(^1\Delta)$ partial pressure below, at least, 30 Torr, most of the gas is diluent and, at a total pressure well-below atmospheric, is not suited for medical or related sea-level applications.

(c) Only a small percentage of the reactive chemicals in the BHP solution are utilized as the BHP flows through the oxygen generator. This results in a large and heavy BHP feed system, or a large and heavy system to recondition or regenerate the partly spent BHP.

As described in "Mixed Marks for the ABL," by Canan in *Aerospace America*, pp. 38-43, August 1999, Earth's gravitational field is required to provide buoyancy for separating the oxygen vapor from the liquid. Prior art SOG devices that rely on gravity for separation of singlet delta oxygen from the reactant flow, such as the BHP droplets in a transverse flow uniform droplet SOG, are not suitable for operation in a space environment.

In addition to prior art SOGs, gas sparger devices are relevant to the production of singlet delta oxygen according to the invention and as discussed more fully below. Gas sparger devices are designed to remove volatile contaminants from a liquid. In a prior art gas sparger, a contaminated liquid is injected, under pressure, onto the inside surface of a porous tube with a circular cross section. Centrifugal force keeps the liquid attached to the inside of the porous walled tube. The liquid follows a helical path as it makes a number of revolutions along the wall. Air, under pressure, is injected from the outside surface of the porous walled tube, through the tube, after which it mixes with the liquid. Most of the volatile contaminants are entrained with the air, which separates from the liquid, due to buoyancy that stems from the centrifugal force. Chemical reactions do not occur in typical gas spargers.

SUMMARY OF THE INVENTION

The present invention provides an improved method and apparatus for generating gas-phase, electronically excited states of oxygen for use in biomedical, chemical, and other applications. Production of $O_2(^1\Delta)$, and consequently $O_2(^1\Sigma)$, is achieved through the reaction of BHP and chlorine in a SOG according to the invention. A dilute basic hydrogen peroxide, or BHP, solution is produced according to the invention by mixing aqueous hydrogen peroxide, water, and aqueous potassium hydroxide, or alternatively sodium hydroxide or a mixture of several hydroxide compounds. The BHP production process is exothermic; therefore, the solution is preferably cooled during preparation and afterward.

Cooled BHP is then injected, under pressure sufficient for a large insertion velocity (typically above about 12 m/s), into a SOG reaction chamber with a concave curved wall. The BHP injection pressure is typically greater than 400 Torr and preferably greater than about 600 Torr. At the point of entry, the solution is a thin, high-speed, liquid layer that flows over the concave wall. The high speed of injection results in a centrifugal force that prevents the aqueous solution from separating from the concave wall. Shortly after the start of the concave wall, chlorine vapor is injected, preferably under pressure sufficient to choke the chlorine vapor flow (i.e. it becomes sonic) in the porous wall and to provide sufficient chlorine for its reaction with BHP. The chlorine is preferably injected through a porous wall that is a small section of the concave wall. Alternatively, the chlorine may be injected under pressure through a converging, two-dimensional nozzle that terminates in a thin slit located in the plane of the concave wall. The injected chlorine vapor, in the form of small bubbles, rapidly mixes and reacts with the BHP solution while the flow is still passing over the concave wall. The reaction with the chlorine produces singlet delta oxygen in the liquid, or frothy, layer.

The singlet delta oxygen forms vapor bubbles. Because of their low density relative to the liquid solution, the bubbles experience a significant pressure gradient that is transverse to the concave wall. This gradient, which is associated with the aforementioned centrifugal force, causes the vapor bubbles to depart the aqueous solution on the side of the liquid, or frothy, layer opposite from where the chlorine vapor enters. Consequently, the chlorine flow rate can be adjusted so that there is little or no contamination in the $O_2(^1\Delta)$ stream. As soon as most, or all, of the generated $O_2(^1\Delta)$ has departed the BHP solution, the spent solution is removed from the reaction chamber by means of an outlet or exhaust duct for the liquid.

The molar flow rate of the chlorine is readily adjusted to maximally utilize the BHP solution. Hence, the concentrations of the active ions and molecules in the BHP solution are significantly depleted. A BHP regenerator system is thus unnecessary.

The salt generated by the BHP-chlorine reaction remains dissolved in the highly dilute aqueous solution. The high-speed aqueous solution passes through the reaction chamber very quickly. Inside the reaction chamber, the temperature of the liquid increases due to exothermic reactions with the chlorine. Because the BHP solution contains added water and is cooled before it enters the reaction chamber, the magnitude of the temperature in the reaction chamber is minimized. This factor, in combination with the reduction of the vapor pressure of the water by the solute, and the few milliseconds that the high-speed solution is located inside the reaction chamber, results in a low contamination level of the $O_2(^1\Delta)$ gas with water vapor. Typically, less than 1% of the water, or deuterated water, in the entering BHP evaporates inside the SOG.

Figure 2:
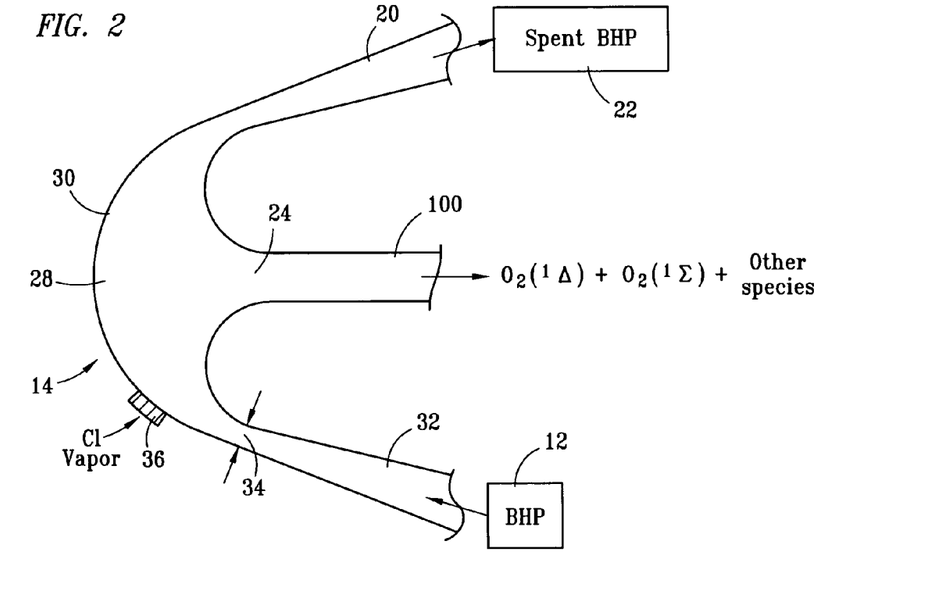
FIG. 2 is a cross-sectional side view of a SOG according to one aspect of the invention.

These preferred features may be used singularly or combined for the efficient generation of $O_2(^1\Delta)$ and $O_2(^1\Sigma)$ in a SOG that has a number of advantages over the prior art. These advantages include:

(1) The SOG is compact and scalable. As shown in FIG. 2, the SOG is a two-dimensional flow device. Its compactness can be ascertained from concave wall 30 in FIG. 2, which nominally has a radius of about 2.5 cm. By increasing, or decreasing, the width of the SOG, in a direction normal to FIG. 2, the excited state flow rates increase, or decrease, proportionately, i.e., the device is readily scaled.

(2) It can operate in a space vehicle or satellite, where gravity is negligible.

(3) Because the partial pressure of the $O_2(^1\Delta)$ plus $O_2(^1\Sigma)$, inside the SOG, can be quite high, in excess of 200 Torr, diluent (preferably argon) can be used, if needed, to bring the operational pressure to 1 atm.

(4) As stated, the $O_2(^1\Delta)$, and therefore the $O_2(^1\Sigma)$, can be generated at an elevated pressure.

(5) The $Cl_2$ is efficiently utilized with up to 100% utilization, while the hydroxide utilization can exceed about 85%. For medical applications, an oxygen stream free of chlorine contamination is preferred.

(6) The excited state oxygen stream is nearly free of chlorine contamination and has a low level of water vapor contamination.

(7) The $O_2(^1\Delta)$ yield, which is the molar ratio of $O_2(^1\Delta)$ to the total oxygen concentration, is important for COIL. Here, it is less important, since Reaction A converts some of the $O_2(^1\Delta)$ to $O_2(^1\Sigma)$. Nevertheless, the current SOG invention is more efficient in producing $O_2(^1\Delta)$ than state of the art SOG devices.

BRIEF DESCRIPTION OF THE DRAWINGS

The accompanying drawings are incorporated into and form a part of the specification to assist in explaining the present invention. The drawings are intended for illustrative purposes only and are not intended as exact representations of the embodiments of the present invention. The drawings further illustrate preferred examples of how the invention can be made and used and are not to be construed as limiting the invention to only those examples illustrated and described. In these drawings, the same reference characters are used throughout the views to indicate like or corresponding parts. The various advantages and features of the present invention will be apparent from a consideration of the drawings in which.

DETAILED DESCRIPTION

The following describes the preferred embodiment of a SOG system and its method of use according to the present invention by reference to FIGS. 1-5. Although the preferred embodiment for the present invention is described, the description is not intended to limit the scope of the invention as defined by the claims. Some details of the SOG and chemical supply systems and their methods of use, including various gauges, fittings, piping, etc. are well known in the art, and as such are neither shown nor described. Even though numerous characteristics and advantages of the present invention are shown and described in the drawings and accompanying text, the description is illustrative only, and changes may be made, especially in matters of arrangement, shape and size of the parts, within the scope of the invention to the full extent indicated by the broad general meaning of the terms used in the claims.

Figure 1:
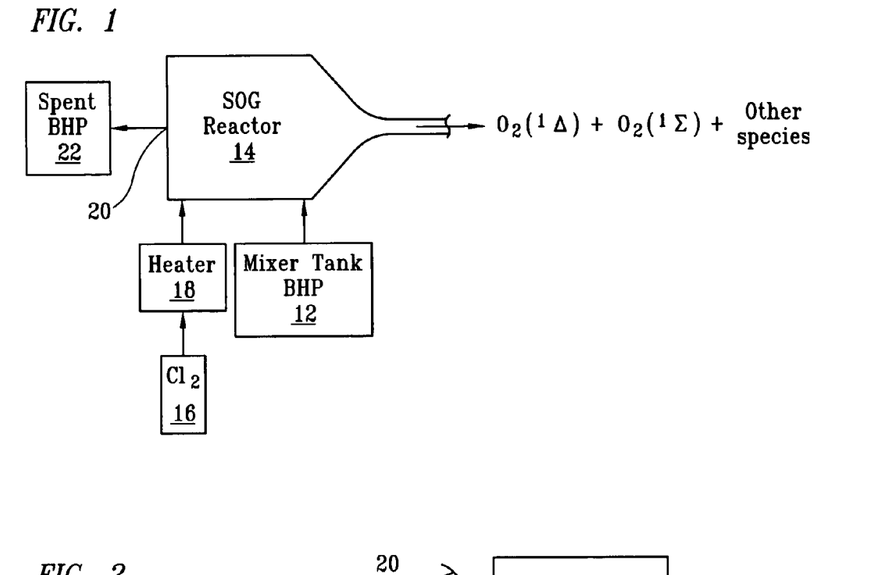
FIG. 1 is a schematic diagram of a SOG system, including BHP and chlorine feed systems, according to one aspect of the invention.

FIG. 1 is a schematic diagram of a SOG system, including BHP and chlorine feed systems, according to one aspect of the invention. The first step in the overall process for generating electronically excited state oxygen in the gas phase is the mixing of liquid water, aqueous $H_2O_2$ and aqueous KOH in mixer 12. Sodium hydroxide or a mixture of several hydroxide compounds may be used in place of potassium hydroxide. The resulting mixture is referred to as a basic hydrogen peroxide (BHP) solution.

The $H_2O_2$ and KOH have approximately the same molar flow rate with a slight excess of $H_2O_2$. The aqueous KOH and aqueous $H_2O_2$ mixed in BHP mixer 12 are commercially available aqueous solutions that are each buffered with additional water. Due to this additional water, the BHP solution is more dilute than is used in prior art systems. Although not necessarily optimum values, the mole ratios of $H_2O_2$, KOH, and $H_2O$ used in a feasibility experiment were approximately 1:1:10, where the $H_2O$ molar value of 10 consists of the aqueous portions of the $H_2O_2$ and KOH solutions plus the added water. In the discussion of molar ratios of $H_2O$, $H_2O_2$, and KOH herein, the $H_2O$ value consists of the aqueous portions of the $H_2O_2$ and KOH solutions plus added $H_2O$. This amount of dilution is higher than prior art practice and may be further increased according to the invention to produce a highly dilute BHP solution to aid in reaction temperature reduction inside the SOG.

The aqueous KOH, aqueous $H_2O_2$, and added water require cooling when they are mixed because of the exothermicity of reactions. Once mixed, and sometime before usage, the BHP should be cooled to a temperature just above its freezing point, preferably to a temperature 1° C. to 5° C. above its freezing point. This temperature is below the freezing point for pure liquid water, since a solute lowers the freezing point. The BHP enters SOG 14 at a temperature where its water vapor partial pressure is below the 4.6 Torr (0.006 atm) value of pure water at 0° C. Due to the use of a relatively dilute BHP solution according to the preferred embodiment of the invention, problems in the prior art with anomalous freezing of the BHP are not encountered.

Chlorine liquid from chlorine supply tank 16 is vaporized in a heater 18 with the chlorine vapor flowing into SOG 14. A pump is usually not required, since the room temperature vapor pressure of liquid chlorine should be sufficient for providing the desired flow rate of chlorine to SOG 14.

The molar flow rate of the chlorine is readily adjusted to maximally utilize the BHP solution by significantly depleting the concentrations of active ions and molecules in the BHP solution. In prior art systems, the molar flow rate of $H_2O_2$ relative to KOH or NaOH for the BHP have approximately the same molar flow rate. The molar flow rate of chlorine is preferably slightly less than that of the KOH or NaOH. Preferably, the chlorine molar flow rate is about 80% to about 95% of the KOH or NaOH molar flow rate, and most preferably about 90% or more of the KOH or NaOH molar flow rate. These molar flow rates can be adjusted to yield 100% or nearly 100% utilization of the chlorine and a high utilization for the hydroxide. Due to the efficient utilization of the reactants, a BHP regeneration or recycling system is not necessary according to the invention.

SOG 14 preferably includes a concave curved wall over which the BHP and chlorine are injected and react to produce singlet delta oxygen. After the reaction, spent BHP solution, comprising salts, small amounts of KOH or NaOH based ions, HCl, and excess $H_2O_2$, exits SOG 14 through exhaust or outlet 20 to a collection tank 22 for proper disposal. Due to the efficient utilization of chemicals according to the invention, it is not necessary to recycle or regenerate the spent BHP solution after the reaction in SOG 14. Preferably, 90% or more of the BHP solution entering SOG 14 comprises non-recycled $H_2O_2$ and hydroxide compounds and most preferably the BHP solution comprises entirely new, non-recycled $H_2O_2$ and hydroxide compounds. Non-recycled refers to chemicals or compounds that have not been recycled from the spent solution exiting SOG 14 through outlet 20. Materials recycled from other processes may be used according to the invention.

FIG. 2 is a cross-sectional side view of a SOG 14 according to one aspect of the invention. BHP and chlorine feed systems are not depicted in FIG. 2. SOG 14 includes a reaction chamber 28 with a concave curved wall 30. A nominal radius of curvature for concave wall 30 is 2.5 cm (1 inch). SOG 14 is a two-dimensional flow apparatus, the dimension of which with respect to the plane of FIG. 2 is arbitrary. Thus, the preferred embodiment of the SOG is compact and fully scalable.

BHP from mixer 12 enters reaction chamber 28 under pressure through a converging nozzle 32 and exits the nozzle at its throat 34 at a considerable speed, typically in excess of 12 m/s. The BHP solution travels along concave wall 30 and remains in substantial contact with this wall. At the point of entry, the BHP solution is a thin, high-speed, liquid layer that may develop into a frothy layer along concave wall 30. It is estimated that the thickness of the liquid layer is less than about 4 mm (0.16 inches), with the frothy layer being about 2 to 4 times thicker than the liquid layer. It is preferred that the fluid layer along concave wall 30 have a thickness of 15 mm (0.6 in) or less. The solution remains a thin layer as it flows over concave wall 30. The high speed of injection results in a centrifugal force that prevents the aqueous solution from substantially separating from the concave wall 30. The centrifugal force is quite large since the BHP is a liquid, the flow speed is large and the radius of curvature of concave wall 30 is small.

Chlorine vapor from chlorine tank 16 and heater 18 is preferably injected under pressure through a porous wall 36 that is a part of concave wall 30. The chlorine injection process is regulated to avoid separating the liquid layer from the concave wall. Alternatively, chlorine can be injected through a converging nozzle with a throat located downstream of BHP nozzle throat 34, as used in the feasibility experiment described below.

Porous wall 36 is located downstream of BHP nozzle throat 34. Most preferably, porous wall 36 is made from a sintered metal, such as stainless steel, or other materials, or porous plastic. It is also preferred that the chlorine flow through porous wall 36 chokes at the exit surface of the wall 36 on the interior of reaction chamber 28. A choked flow insures a nearly uniform distribution of chlorine vapor over the exit surface of porous wall 36. It also provides useful momentum for the chlorine that will aid both the chlorine/BHP mixing and the subsequent removal of the singlet delta oxygen from the solution. Choking also enables better control of the chlorine molar flow rate. The magnitude of the chlorine molar flow rate, which is preferably slightly less than the molar flow rate of KOH or NaOH, establishes the magnitude of the surface area of porous wall 36 as will be understood by those of skill in the art.

The pressure of the chlorine at the exit surface of porous wall 36 must be approximately equal to that of the BHP flowing along concave wall 30. Due to the centrifugal force along concave wall 30, the BHP pressure at the wall exceeds that in a plenum. To match the BHP wall pressure, the chlorine vapor first goes through an expansion as the flow adjusts from the constricted flow area inside the porous wall 36 to the external surface of the porous wall inside reaction chamber 28. Before the flow exits the porous wall 36, it may go through a compression whose downstream pressure matches or approximates the BHP wall pressure.

The injected chlorine vapor, in the form of small bubbles, rapidly mixes and reacts with the BHP solution while the flow is still passing over the concave wall. The chlorine vapor bubbles are approximately the same size as the pores in porous wall 36. The chlorine bubbles are subjected to a large shearing force as they enter the high-speed BHP layer. The shearing force distorts the chlorine bubbles and helps result in a very large contact surface area. The liquid-gas contact surface area according to the invention is significantly higher than in prior art SOG devices. The chlorine and BHP react and produce $O_2(^1\Delta)$ in the liquid, or frothy, layer. According to the invention, it is not necessary to add any diluents, such as helium, to SOG 14, although diluents may be added. If added, the diluents are preferably added with the chlorine vapor through porous wall 36.

When a one atmosphere SOG oxygen pressure is not feasible, a diluent such as helium, nitrogen, or argon is used. This would be the case when the delivery system, see FIG. 3, results in significant $O_2(^1\Delta)+O_2(^1\Sigma)$ deactivation. For biological or chemical weapon deactivation, argon is preferred since it results in a gas mixture with negative buoyancy, thereby increasing the contact time between the excited oxygen and its target. In time, possibly several hours, the excited oxygen spontaneously deactivates to ordinary oxygen. Regardless of the application, the excited oxygen, with or without diluent, is environmentally benign. With argon diluent, the device may be used outdoors, as well as indoors, for the decontamination of biological or chemical weapons.

The singlet delta oxygen forms vapor bubbles. Because of their low density relative to the liquid solution, the bubbles experience a significant pressure gradient, or buoyancy force associated with the centrifugal force of flow along concave wall 30, that is transverse to concave wall 30. This buoyancy force causes the low-density vapor bubbles to depart the aqueous solution on the side of the liquid, or frothy, layer opposite from where the chlorine vapor enters through porous wall 36. The centrifugal force also permits SOG 14 to operate in a zero-gravity or low gravity environment. This arrangement in combination with the high percentage utilization of 100% or nearly 100% of the chlorine in the BHP-chlorine reaction, results in very little or no chlorine contamination of the $O_2(^1\Delta)$ stream. The $O_2(^1\Delta)$ stream departs SOG reaction chamber 28 through an exit 24 into the delivery system 100.

Many factors control the rate at which the $O_2(^1\Delta)$ departs the liquid solution to the exit or duct 100. As the reactants pass through SOG 14 very quickly, it is important that the $O_2(^1\Delta)$ depart the liquid solution quickly so that it does not remain entrained in the solution as the solution is exhausted to the collection tank 22. These factors include the injected thickness of the BHP layer, the injection speed of the BHP, the average pore size in porous wall 36, the radius of curvature of concave wall 30, which is nominally around 2.5 cm (1 in), the angular extent of concave wall 30, which is preferably less than 160° in extent, and the pressure inside reaction chamber 28. These factors are chosen iteratively, in conjunction with other design and performance constraints as will be understood by those of ordinary skill in the art. For instance, sintered metal porous sheets are available in a range of thicknesses with a range of average pore sizes. As the average pore size decreases, the pressure change, for a given flow rate of chlorine, across the porous wall increases.

As soon as most, or all, of the generated $O_2(^1\Delta)$ has departed the BHP solution, the spent solution is removed from reaction chamber 28 by means of an exhaust duct or outlet 20. The spent solution is comprised of salt byproducts (KCl or NaCl), a small quantity of KOH or NaOH based ions, HCl, and excess $H_2O_2$. It is preferred to remove the spent solution as quickly as possible with a smooth inlet for exhaust duct 20 that avoids splashing or aerosol formation that could contaminate the $O_2(^1\Delta)$ vapor stream. A suction pump in the exhaust may be used, if necessary, to assist with removal of the spent solution. The spent solution is stored in collection tank 22 (as shown in FIG. 1) for proper disposal, no BHP regeneration or recycling system is needed according to the invention.

The salt generated by the BHP-chlorine reaction remains dissolved in the highly dilute aqueous solution. The high-speed aqueous solution passes through reaction chamber 28 very quickly, preferably in fewer than about 20 milliseconds, more preferably in fewer than about 10 milliseconds, and most preferably in fewer than about 5 milliseconds. Inside reaction chamber 28, the temperature of the liquid increases due to exothermic reactions with the chlorine. Because the BHP solution contains added water and is cooled before it enters the reaction chamber, the magnitude of the temperature in the reaction chamber is minimized. A finite amount of time is required for the water vapor partial pressure to reach its equilibrium value with the post-reaction temperature of the aqueous solution. As the reactants pass through reaction chamber 28 very quickly, there is insufficient time for the evaporation of liquid water to establish an equilibrium value for the water vapor at the post-reaction temperature, in the singlet delta oxygen exhaust stream. This factor, in combination with the reduction of the vapor pressure of the water by the solute, the energy required for the evaporation process, and the few milliseconds that the high-speed solution is located inside the reaction chamber, results in a low contamination level of the $O_2(^1\Delta)$ gas stream with water vapor. According to the invention, it is not necessary to use a water vapor trap prior to exit 24, but a water vapor trap may be used if desired.

The gases exiting 24 consist of the desired $O_2(^1\Delta)$ and $O_2(^1\Sigma)$, a small amount of water vapor, some $O_2(^3\Sigma)$, a very small amount, if any, of chlorine vapor, and diluent, if added. The mole fraction of $O_2(^1\Delta)$ plus $O_2(^1\Sigma)$ relative to the total oxygen depends on the initial partial pressure of $O_2(^1\Delta)$ and the residence time of the $O_2(^1\Delta)$ and $O_2(^1\Sigma)$ in the SOG. If this residence time is no more than 0.5 ms, then in excess of 75% of the total oxygen exiting the SOG, whose pressure is 1 atm, is $O_2(^1\Delta)$ and $O_2(^1\Sigma)$. In this circumstance, no added diluent is needed provided the excited oxygen is not excessively deactivated in the delivery system downstream of the SOG. If the residence time is 1.94 ms, then 75% of the total oxygen exiting the SOG is $O_2(^1\Delta)$ or $O_2(^1\Sigma)$ and the initial partial pressure of the $O_2(^1\Delta)$ is 200 Torr. Approximately 560 Torr of diluent is required for 1 atm pressure. The above are conservative theoretical estimates. Actual operation should not require in excess of 75% of the departing oxygen be $O_2(^1\Delta)$ and $O_2(^1\Sigma)$. Moreover, as the 75% fraction decreases, the residence time rapidly increases.

Because of its compact, two-dimensional scalable configuration the SOG according to the invention is preferably located in close proximity to the desired delivery location for the electronically excited oxygen. The $O_2(^1\Delta)$ generated in the BHP-chlorine reaction along the concave wall 30 need only travel a few centimeters, preferably about 5 cm (1.97 inches) or less, after departing the BHP-chlorine solution, which is preferably less than about 15 mm thick along concave wall 30, to reach the exit 24 in the preferred embodiment. As seen in FIG. 2, exit 24 is preferably located opposite curved wall 30, such that the distance between curved wall 30 and exit 24 is less than about 10 cm and preferably less than 5 cm. Consequently, $O_2(^1\Delta)$ and $O_2(^1\Sigma)$ vapor are at an elevated pressure for only a few milliseconds, and do not have time to collisionally deactivate to any significant extent. The reduction in contaminants in the $O_2(^1\Delta)$ stream and the close proximity of the SOG to exit 24 and ultimately the desired delivery location in the preferred embodiment of the invention make it feasible to produce $O_2(^1\Delta)$ and $O_2(^1\Sigma)$ at an elevated pressure.

A SOG according to a preferred embodiment of the invention yields $O_2(^1\Delta)$ at a higher rate than prior art SOGs. Due to deactivation while the $O_2(^1\Delta)$ is dissolved in the BHP solution, deactivation of walls and the dimol and pooling reactions for $O_2(^1\Delta)$, the yield of $O_2(^1\Delta)$ at the desired delivery point in prior art systems, such as the throat of a laser nozzle in prior art COIL systems does not exceed about 50%. Higher yield values are often cited for prior art COIL devices, but these are upstream of the laser's nozzle throat. The dimol and pooling reactions are the dominant deactivation mechanisms and have driven prior art SOG systems to operate at low partial pressures for the $O_2(^1\Delta)$. However, according to the invention, deactivation of $O_2(^1\Delta)$ according to the other mechanisms is reduced. For instance, the $O_2(^1\Delta)$ rapidly departs the BHP solution inside the reaction chamber, there is no need for a water vapor trap, and the generated $O_2(^1\Delta)$ need only travel a short distance to the SOG's exit. These factors allow a SOG according to the invention to operate at high pressures while still resulting in a sufficient mole fraction of $O_2(^1\Delta)$ and $O_2(^1\Sigma)$ at exit 24.

In addition to operation at a high pressure and with improved yield, the SOG according to the invention has a number of major advantages over prior art SOG devices. These include: (1) it is scalable, (2) it can operate in a zero-gravity or low gravity environment, (3) no added diluent or buffer gas is required, (4) the chemicals are efficiently utilized and (5) the $O_2(^1\Delta)$ stream is substantially free of chlorine and water vapor contamination. For non-COIL applications, zero-gravity operation may not be of interest, water vapor contamination should be minimized, and the use of diluent, which can be helium, nitrogen, argon, etc., is not an issue. If a diluent is used, argon is preferred because of its very slow rate of deactivation of excited oxygen species and its negative buoyancy.

As indicated in the prior discussion, $O_2(^1\Delta)$ is effective in destroying diseased tissue and, in general, in destroying pathogens. One aspect of this process is the deposition in the target cell or virus of the 94.2 kJ/mol of electronic energy. In this regard, $O_2(^1\Sigma)$ may prove to be more effective, because of its greater excitation energy. The effectiveness of $O_2(^1\Sigma)$, however, is not known at this time. At any rate, if $O_2(^1\Sigma)$ is to be used, it would preferably be in a relatively dry gaseous mixture or the BHP would preferably use deuterated water.

Typically, diseased tissue contains little, if any, healthy tissue, instead the diseased tissue is imbedded in a matrix of otherwise healthy tissue. When $O_2(^1\Delta)$ and $O_2(^1\Sigma)$ are delivered to the diseased tissue in the gas phase, surrounding healthy tissue may come under attack. This may not prove detrimental if the rate of reaction is substantially less than on diseased tissue. Alternatively, it might be possible to substantially screen or shield the healthy tissue from contact with the excited oxygen, for example, a cream that excited oxygen does not penetrate or other mechanical means of shielding healthy tissue.

Gas-phase $O_2(^1\Delta)$ and $O_2(^1\Sigma)$ may be useful in the sterilization of medical instruments and equipment, such as catheters and pacemakers, and for the sterilization of air ducts, hoses, other passageways, or other confined or enclosed spaces. These might be the ducts that bring in outside air into the operating rooms of a hospital or the operating room itself. Gas-phase sterilization for both instruments and ducts should prove beneficial relative to liquid sterilization because of a gas's ability to penetrate small fissures and cracks. This penetrating ability also might be important in the treatment of diseased tissue.

One strategy that allows bacteria to survive antibiotics is aggregations of dangerous microbes called biofilms. According to the prior art, this persistence (rather than actual resistance) is responsible for the failure of antibiotic treatments, especially when the biofilm is attached to foreign bodies, such as prostheses or catheters. Exposure to gas-phase, electronically excited oxygen may prove an effective way for destroying these persistent biofilms.

Electronically excited gas-phase oxygen should prove particularly effective for the destruction of chemicals and pathogens used in warfare or terrorist attacks. Electronically excited oxygen is exceptionally reactive, and, because of its ability to deposit energy, should prove effective in treating a very broad spectrum of toxic chemicals and pathogens by neutralizing or otherwise deactivating those agents. In this regard, it should prove more cost effective than more specialized or selective approaches. A major advantage of a broad-spectrum approach is that the difficult and time-consuming process of toxic agent identification can be bypassed.

As an illustration, consider a missile of small, medium, or large size, with a comparable range, that is intercepted during its trajectory and destroyed. The part of the missile containing its payload, however, may continue in a modified trajectory and impact somewhere in the targeted region. A chemical or biological payload, of unknown type, may still prove lethal and very dangerous. A quick response, using a portable instrument, with a broad-spectrum agent that is effective against both chemical and biological weapons, is desirable. Moreover, the agent should have a transitory lifetime so that it does not in itself become a problem. A sprayed gaseous layer containing electronically excited oxygen that blankets the impact area may prove effective and efficient for the destruction of the biological pathogen or chemical agent or species. The SOG 14 and related chemical delivery systems depicted in FIG. 1 may be used as a portable or mobile treatment system to treat the chemical species or pathogen in the field. The SOG 14 and related chemical delivery systems may also be used as a portable or mobile treatment system for medical treatments and sterilization so the device is capable of being moved to the location of the patient or the location of the item or material to be treated or sterilized. The SOG 14 may be transported or mounted in a van, truck, trailer or cart to the site of the biological or chemical agent or species to be treated so that the excited oxygen may be delivered via delivery system 100. Any form of transportation may be used for the portable SOG according to the invention provided it is capable of carrying the SOG 14 and related chemical delivery systems based on its size and weight. In the case of treating biological or chemical agents it is preferable to add a high molecular weight, inert diluent (preferably argon) to the excited oxygen to help delay the spreading and buoyancy of the excited oxygen gas. Such a diluent is particularly preferred when treating biological or chemical agents in the outdoors or in other large, open areas. The transitory nature of the excited oxygen is evident. An additional benefit might be high temperature combustion between the enriched oxygen cloud, compared to air, and the ambient combustible surface where the agent is located.

Figure 3:
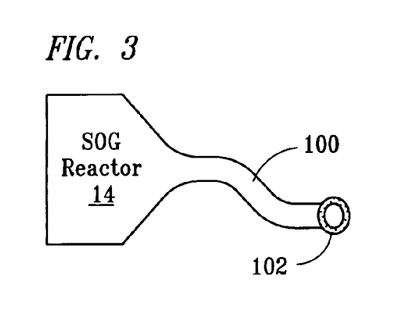
FIG. 3 is a schematic diagram of a SOG and electronically excited state oxygen delivery system, preferably for medical applications, according to one aspect of the invention. A somewhat similar configuration is used for sterilization and weapon decontamination.

FIG. 3 a schematic diagram of a SOG and electronically excited state oxygen delivery system according to one aspect of the invention. The gas-phase $O_2(^1\Delta)$ and $O_2(^1\Sigma)$ molecules are transported, along with gaseous byproducts, from a SOG unit to a targeted site through a delivery system. The delivery system includes some means of directing the flow of excited oxygen from the SOG to the target site, such as conduit 100, which may be a hose or duct, and, in some cases, preferably a conduit, duct or hose coupled with a porous o-ring 102. The conduit, hose, or duct may be of varying lengths provided it is capable of directing excited oxygen from the SOG to the target. Preferably, conduit 100 is made of flexible material and terminates in an open end, which may be placed flush with or near diseased tissue or the surface or area requiring sterilization or treatment. Surrounding the open end is preferably an annular O-ring 102. O-ring 102 is preferably porous and made of flexible rubber or plastic, but other suitable materials may be used. The porous O-ring 102 is placed adjacent to the tissue or surface to be treated and allows the spent gas to pass through it into the atmosphere. Depending on the application, other modes of delivery may be used according to the invention.

If the length of the hose is quite short, preferably less than 30 cm, then the SOG may operate at slightly above atmospheric or ambient pressure and without diluent. As the length of the hose increases, particularly if lengths in excess of 30 cm are used, a diluent (preferably He, $N_2$, or argon) is used because of deactivation and the total oxygen partial pressure in the SOG and throughout the delivery system is sub-atmospheric. In such a situation, the gas at the end of hose 100 would then consist of a mixture of $O_2(^3\Sigma)$, $O_2(^1\Delta)$, $O_2(^1\Sigma)$, $H_2O$ (or deuterated $H_2O$), and diluent at a pressure slightly above one atmosphere. The mole fraction of $O_2(^1\Sigma)$ may be small because of $H_2O$ deactivation. However, use of the preferred SOG according to the invention reduces the amount of water vapor exiting the SOG with the excited oxygen. It is not necessary to use a water vapor trap at or downstream of SOG exit 24; however, if $O_2(^1\Sigma)$ is especially useful in the desired application, a cold trap, or equivalent system for the removal of water vapor, may be used at exit 24 or elsewhere in hose 100. Alternatively, deuterated water can be used.

A SOG according to the invention, but particularly for use in a COIL system, was developed and tested in a feasibility experiment. FIG. 4 is a schematic diagram of a SOG system according to a feasibility experiment and FIG. 5 is a cross-sectional view of the test apparatus used in the feasibility experiment. Details regarding the amounts of reactants used, flow rates, part sizes, etc. described herein are illustrative of the preferred values for operation of a test-scale SOG in the feasibility experiment and do not limit the scope of the invention as claimed. Additionally, some details of the SOG and chemical supply systems and their methods of use in the feasibility experiment, including various gauges, fittings, piping, etc. are well known in the art, and as such are neither shown nor described.

FIG. 4 is a schematic diagram of a SOG system, including BHP and chlorine feed systems, according to a feasibility experiment for the present invention. The test apparatus consists of a BHP preparation system, a BHP feed system, a chlorine feed system, a SOG reactor 38, an exhaust system for the generated $O_2(^1\Delta)$ gas, and an exhaust system for the spent aqueous solution. The test materials are high-pressure nitrogen, a liquid nitrogen dewar, 30% aqueous $H_2O_2$, 45% aqueous KOH, liquid chlorine, distilled water, and tap water. All materials are commercially available.

Water/nitrogen preliminary flow tests are first performed with nitrogen replacing chlorine and water replacing BHP. High-pressure nitrogen from nitrogen gas tank 40 is used to purge chlorine line 42 and tap water flows through BHP line 44 to perform this preliminary flow test.

BHP is prepared in a batch by first pouring distilled water into mixer 46, after which an aqueous $H_2O_2$ solution is added from $H_2O_2$ tank 48. Aqueous KOH is then allowed to slowly drip into mixer 46 from KOH tank 50. Both the $H_2O_2$ and KOH solutions are pre-cooled in a refrigerator. During mixing with the KOH, the contents of mixer 46 are cooled with liquid nitrogen from nitrogen tank 52. Liquid nitrogen flows through a heat exchanger 54 with vertical copper tubing for the cold nitrogen. The BHP temperature is monitored during preparation, and the KOH drip rate is adjusted to avoid overheating the BHP solution.

After the BHP has been prepared, a positive displacement pump 56, in BHP line 44 between mixer 46 and SOG 38, pumps BHP to SOG 38. Liquid chlorine tank 58 includes an eductor tube, which provides liquid chlorine to a heater 60 that gasifies it. Chlorine vapor passes through line 42 to SOG 38. The time duration of a test is determined by the amount of BHP that has been prepared and the flow rate of BHP during a test run.

FIG. 5 is a cross-sectional side view of a SOG 38 and particularly reaction chamber 62 of SOG 38 according to a feasibility experiment for the present invention. Side walls 64 of SOG 38 are 0.25-inch thick, clear acrylic plates with a number of slotted holes 66 that allow for adjustment of four aluminum inserts 68 that provide flow paths for the BHP and chlorine reactants. The width of the inserts 68 is 1-inch, and the flow paths between side walls 64 are two-dimensional. The inlet and exhaust ducting, such as exhaust duct 70, is rectangular in cross-section, but the transition to a circular configuration is easily performed. Thus, the 1-in dimension is readily increased to any desired length; which establishes the scalability of a SOG according to the invention. The SOG 38 depicted in FIG. 5 is only slightly smaller than the actual test device. This verifies the compactness of a SOG according to the invention.

Chlorine vapor flows through a converging nozzle 72, entering reaction chamber 62 through a narrow two-dimensional slit, or throat 74. Although it is preferred to use a porous wall to inject the chlorine into the reaction chamber according to the invention, a nozzle configuration, as used in the feasibility experiment, may also be used. The BHP aqueous solution flows downward through a converging nozzle 76, entering reaction chamber 62 through a narrow, two-dimensional slit, or throat 78. The chlorine vapor enters reaction chamber 62 shortly after the BHP solution enters. The vapor and liquid mix and flow along a concave-curved wall 80. The reactant solution impacts an angled wall 82 that directs the liquid flow into an exhaust duct 70. A vapor exhaust 84, for exhausting $O_2(^1\Delta)$ gas, is located on the top side of SOG 38. The solution exiting through exhaust 70 flows to a collection tank 86 (as shown on FIG. 4). A 1.5 hp motor is located in the lid of the collection tank. The fan on the motor provides a small suction pressure that assists the flow of the spent liquid out of SOG 38.

In a feasibility experiment for a SOG according to the invention, the BHP solution comprises a mixture of about 1 gallon (3.79 L) of distilled water, 1 gallon (3.79 L) of 30% aqueous $H_2O_2$, and 0.8 gallons (3 L) of 45% aqueous KOH. These volumes translate into $H_2O_2$, KOH, and $H_2O$ molar ratios of approximately 1:1:10, where the $H_2O$ value includes the aqueous portions of the $H_2O_2$ and KOH solutions and the added water. In contrast to BHP solutions used in prior art SOGs, this BHP solution is dilute.

Figure 4:
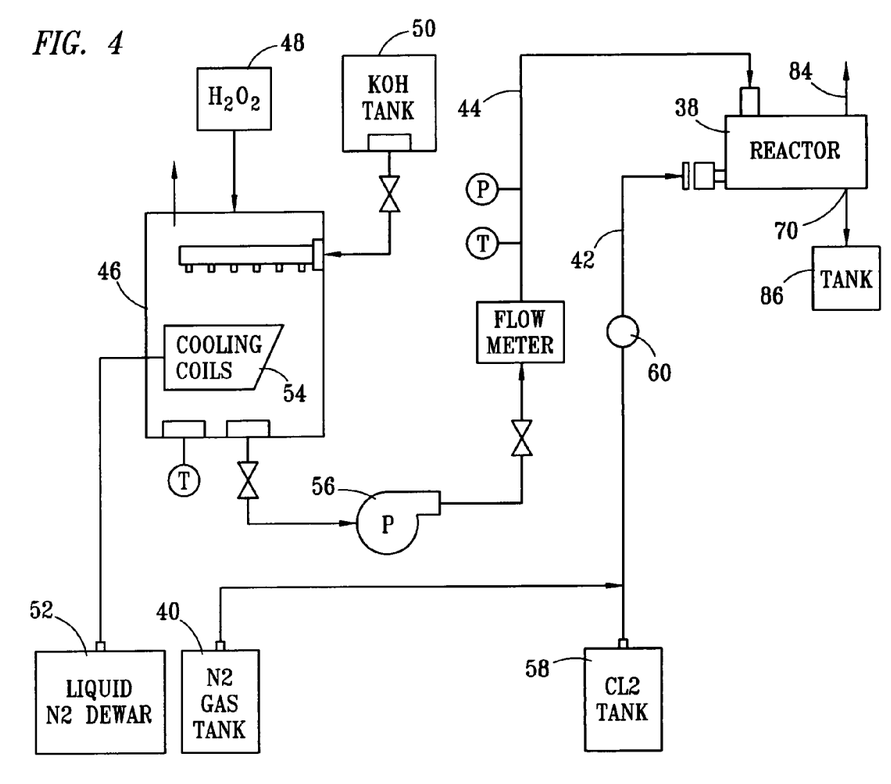
FIG. 4 is a schematic diagram of a SOG system, including BHP and chlorine feed systems, according to a feasibility experiment for the present invention.

The $H_2O_2$ and KOH solutions are pre-cooled in a refrigerator to a temperature below 32° F. During BHP preparation, which took about 50 minutes during the feasibility experiment, the BHP temperature is limited to a maximum value of 36° F. The BHP is preferably cooled not only during its preparation, but further cooled, if necessary, to a temperature slightly above its freezing point before injection into the reactor. Anomalous freezing of the BHP solution that has been problematic in prior art systems does not occur according to the invention due to the use of a relatively dilute BHP solution, such as used in the feasibility experiment. A test run begins within a few minutes after BHP preparation is completed. For the feasibility experiment, positive displacement pump 56 is set for a BHP flow rate of about 1.7 gpm (6.4 L/min), which provided a run time of about 1.5 minutes.

Figure 5:
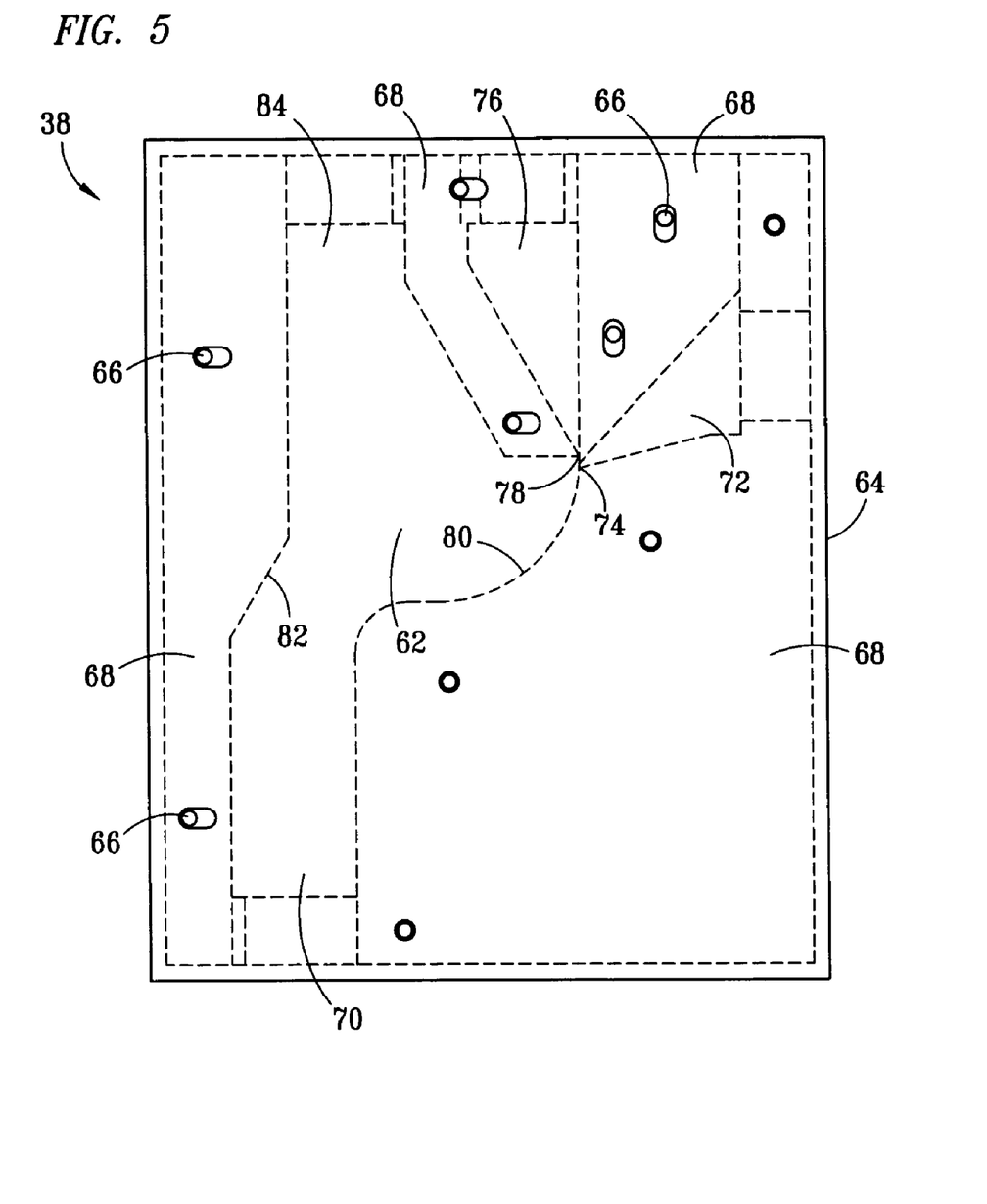
FIG. 5 is a cross-sectional side view of a reaction chamber of a SOG system according to a feasibility experiment for the present invention.

The slit 78 at the exit of BHP nozzle 76 is about 0.02 inches (0.05 cm), while the slit 74 at the exit of chlorine nozzle 72 is about 0.06 inches (0.15 cm). Vapor exhaust 84 is throttled such that the vacuum pressure inside reaction chamber 62, during the test, is only about 6-inches of water, or 0.21 psi, below the ambient atmospheric pressure. This translates to a reaction chamber pressure of about 14.5 psi (750 Torr) without the use of any gaseous diluents, which is significantly higher than typical prior art systems.

The presence of $O_2(^1\Delta)$ in SOG 38 in the feasibility experiment described was confirmed by a visual inspection through the clear side walls of SOG 38. An intense red dimol emission, from the liquid and from the vapor, confirmed the reaction produced gaseous $O_2(^1\Delta)$. The emission was noted during the experiment immediately after the BHP and chlorine began mixing. This indicates the rapidity with which the reaction takes place.

In addition to the parameters of the feasibility experiment described above, nominal values for key parameters of a SOG according to the invention are as follows. These values are not considered to be minimums, maximums, or optimum values and may be adjusted according to the desired scale of the system. A 2.5 cm width for the SOG coupled with a radius of curvature for the concave wall of 2.5 cm (1 inch), a BHP nozzle throat of about 1 mm (0.04 in), and a SOG exit height of about 1.58 cm (0.62 in). For a 2.5 cm width dimension, the chemical flow rates are:

| Constituent | Weight % of Aqueous Solution | Mass Flow Rate, kg/s |
|---|---|---|
| aq. $H_2O_2$ | 35 | 0.1066 |
| aq. KOH | 45 | 0.1368 |
| added $H_2O$ | — | 0.2508 |
| Chlorine | — | 0.0350 |

An improved SOG and its method of use are described according to the invention. It will be understood by those of skill in the art that variations in the components or arrangement of components described may be made within the scope of the invention.

The invention claimed is:

1. A method of treating a chemical species or pathogen, the method comprising:
    feeding a flow of basic hydrogen peroxide (BHP) to a Singlet Delta Oxygen generator (SOG) having an inner wall that includes a curved inner wall portion so that the BHP flows as a liquid layer along a surface of the inner wall of the SOG;
    contacting the liquid layer with chlorine to produce Singlet Delta Oxygen;
    separating Singlet Delta Oxygen from the liquid layer by utilizing centrifugal forces generated by flowing the liquid layer along a surface of the curved inner wall portion of the SOG;
    exhausting the Singlet Delta Oxygen through an outlet at a total pressure that is greater than ambient pressure and exhausting the liquid layer via a different outlet;
    directing the exhausted flow of Singlet Delta Oxygen through a duct; and
    contacting the chemical species or pathogen with Singlet Delta Oxygen.

2. The method of claim 1, wherein the step of directing further comprises introducing a diluent to the flow of Singlet Delta Oxygen at a partial pressure sufficient to provide a total pressure that is greater than ambient pressure.

3. The method of claim 2 wherein the diluent is argon.

4. The method of claim 1 wherein the pathogen is a tumor.

5. The method of claim 1 wherein the pathogen is a biofilm.

6. The method of claim 1 wherein the chemical species or pathogen is a chemical or biological weapon.

7. The method of claim 6 wherein the chemical species or pathogen is treated without first identifying the species or pathogen.

8. The method of claim 1 wherein the SOG is external to the chemical species or pathogen being treated.

9. The method of claim 1, wherein the method further comprises transporting the SOG to the chemical species or pathogen.

10. The method of claim 1, wherein the step of directing further comprises directing the flow of Singlet Delta Oxygen through a hose.

11. The method of claim 1, wherein the step of contacting to produce Singlet Delta Oxygen comprises providing stoichiometrically sufficient moles of chlorine to react with about 80% to about 95% of hydroxide in the fluid fed to the SOG.

12. The method of claim 1, wherein the step of feeding so that the BHP moves as a liquid layer comprises feeding so that the liquid layer has a thickness about 15 mm or less.

13. The method of claim 1, wherein the contacting with chlorine comprises introducing, and rapidly mixing, chlorine vapor as bubbles into the liquid layer and reacting BHP with the chlorine vapor.

14. The method of claim 1, wherein the step of feeding comprises feeding at a pressure greater than about 400 Torr.

15. The method of claim 1, wherein the step of feeding comprises feeding at a pressure greater than about 600 Torr.

16. The method of claim 1, further comprising, prior to the step of feeding a flow of BHP, cooling the BHP to a temperature where the water vapor pressure thereof is below 4.6 Torr.

17. The method of claim 1, wherein the step of exhausting comprises exhausting a fluid comprising Singlet Delta Oxygen that is substantially free of chlorine.

18. The method of claim 1, wherein a time period from the step of feeding the fluid to the step of exhausting the liquid layer is less than about 20 milliseconds.

19. A method of treating a chemical species or pathogen, the method comprising:
- feeding a fluid comprising basic hydrogen peroxide (BHP) and hydroxides at a pressure greater than about 400 Torr to a Singlet Delta Oxygen generator (SOG) having an inner wall, the inner wall including a curved inner wall portion, so that the BHP moves as a liquid layer along the inner wall of the SOG;
- flowing the fluid as a liquid layer in contact with and along the inner wall of the SOG;
- injecting chlorine vapor into the SOG while flowing the fluid as a liquid layer;
- contacting the fluid flowing as a liquid layer with the injected chlorine vapor and thereby mixing the chlorine vapor in the form of chlorine bubbles in the liquid layer, to react to produce Singlet Delta Oxygen;
- utilizing centrifugal forces generated when flowing the liquid layer along the curved inner wall portion of the SOG to separate Singlet Delta Oxygen from the liquid layer;
- exhausting a fluid product comprising Singlet Delta Oxygen, substantially free of chlorine, through an outlet of the SOG proximate the curved inner wall portion of the SOG; and
- contacting the chemical species or pathogen with the fluid product.

20. The method of claim 19, wherein the step of injecting chlorine comprises injecting chlorine uniformly along a length of the SOG.

21. The method of claim 19, wherein the step of injecting chlorine comprises injecting sufficient moles of chlorine to react with about 80% to about 95% of the molar flow rate of hydroxide in the fluid fed to the SOG.

22. The method of claim 19, wherein the step of feeding comprises feeding at a pressure greater than about 600 Torr.

23. The method of claim 19, further comprising, prior to the step of feeding a flow of BHP, cooling the BHP to a temperature where the water vapor pressure thereof is below 4.6 Torr.

* * * * *